United States Patent
Charash (10) Patent No.: US 7,037,261 B2
(45) Date of Patent: *May 2, 2006

(54) FUNDAMENTAL FREQUENCY ESTIMATION OF ELECTRO-ISLET GRAPHY

(75) Inventor: Dan Charash, Haifa (IL)

(73) Assignee: Carmel Biosensors Ltd., Haifa (IL)

( * ) Notice: Subject to any disclaimer, the term of this patent is extended or adjusted under 35 U.S.C. 154(b) by 0 days.

This patent is subject to a terminal disclaimer.

(21) Appl. No.: 10/941,370

(22) Filed: Sep. 15, 2004

(65) Prior Publication Data

US 2005/0033126 A1 Feb. 10, 2005

Related U.S. Application Data

(63) Continuation of application No. 09/530,684, filed as application No. PCT/US99/11973 on May 28, 1999, now Pat. No. 6,884,215.

(60) Provisional application No. 60/087,026, filed on May 28, 1998.

(51) Int. Cl.
    *A61B 5/00* (2006.01)
(52) U.S. Cl. .................. 600/309; 600/365; 600/407
(58) Field of Classification Search ............... 600/300, 600/309, 345, 347, 365, 407; 128/897, 898
    See application file for complete search history.

(56) References Cited

U.S. PATENT DOCUMENTS

| 5,101,814 | A | | 4/1992 | Palti |
| 6,093,167 | A | * | 7/2000 | Houben et al. ............. 600/365 |
| 6,884,215 | B1 | * | 4/2005 | Charash ..................... 600/365 |

OTHER PUBLICATIONS

Simmons, A.M. and M. Ferragamo, "Periodicity extraction in the anuran auditory nerv.1 "Pitch-shift" effects." Journal of Comparative Physiology A Sensory, Neural and Behavioral Physiology. 172(1): 57-69 (Feb. 1993).

* cited by examiner

*Primary Examiner*—Eric F. Winakur
(74) *Attorney, Agent, or Firm*—Darby & Darby (57) ABSTRACT

The fundamental frequency of EIG events is determined directly, without first detecting the events themselves. Use is made of an analysis window containing more than one event (3–5). Techniques (1–8) are utilized which are somewhat similar to those utilized to detect, and estimate pitch in speech processing. The invention is based on two important biological discoveries. The first is that the EIG is generated by a functional pace maker. The second is that the EIG signal is quasi-periodic most of the time. The use of pitch detection algorithms is based on the essentially quasi-periodic nature of the EIG signal. Quasi-periodic means that the intervals between successive events are not exactly identical, but may vary slightly, that the amplitude and shape of successive events may also exhibit some variance.

15 Claims, 9 Drawing Sheets

FUNDAMENTAL FREQUENCY ESTIMATION OF ELECTRO-ISLET GRAPHY

This patent application is a continuation of prior U.S. patent application Ser. No. 09/530,684, filed Jul. 20, 2000 now U.S. Pat. No. 6,884,215.

FIELD OF THE INVENTION

The present invention relates generally to methods and systems for processing electro-physiological signals and, more particularly, concerns the detection and analysis of electrical activity related to blood glucose concentration.

BACKGROUND OF THE INVENTION

Blood glucose level monitoring is of great importance for diabetics. Continuous monitoring of the glucose level can greatly reduce the medical complications, that are caused by metabolic imbalance.

The Islets of Langerhans are located in the pancreas, and are responsible for the manufacture of insulin in the human body. An islet is a cluster of many cells. The Beta cells within the islets respond to glucose in bursts of electrical activity. The use of such islets, derived from the pancreas of donor animals, in a blood glucose monitor is disclosed in U.S. Pat. No. 5,101,814. Electro-Islet-Graphy (EIG) is the measurement of the electrical activity of the islets of Langerhans. The present invention utilizes EIG to provide a continuous blood glucose level sensor.

Studies demonstrate a clear correlation between the fundamental frequency of the EIG signal, and the glucose level in the medium surrounding the islet. Hence, the estimation of the fundamental frequency of Electro-Islet-Graphy is of significant practical value.

The fundamental frequency is defined as the frequency of the "events" of the EIG. An "event" is believed to represent the synchronized electrical activity of the cells in the islet. By analogy to an ECG, an "event" in EIG is comparable to a the heart cycle (the PQRST comlex).

Although it is believed that EIG processing has not been performed by any entity but the owner the present patent application, one might attempt to detect the events directly, and then to calculate the fundamental frequency. The problem with this approach is that the shape and size of EIG "events" varies greatly, and therefore reliable and robust event detection is difficult to achieve.

In accordance with the present invention, the fundamental frequency of EIG events is determined directly, without first detecting the individual events themselves. All these algorithms must use an analysis window containing more than one event. The present invention utilizes techniques similar to those utilized to detect and estimate pitch in speech processing The invention is based on two important biological discoveries. The first is that the EIG is generated by a functional pace maker. The second is that the EIG signal is quasi-periodic most of the time. Pitch detection algorithms are used, because of the essentially quasi-periodic nature of the EIG signal. By quasi-periodic we mean that (1) the intervals between successive events are not exactly identical, but may vary slightly and (2) the amplitude and shape of successive events may also exhibit some variance.

Several pitch detection algorithms were tested. Three of them achieved good results: Autocorrelation, Segmented Autocorrelation and Harmonic Peaks analysis. The preferred embodiments of the invention focus on algorithms that are based on the Autocorrelation methods.

The preferred version of the algorithm comprises the following steps:

Detection of the non-EIG signals. The signal may include non-EIG segments, such as artifacts and silences. The signal is scanned and the non-EIG segments are marked and ignored.

The signal is divided into overlapping analysis windows, each four seconds long and each has a 75% overlap with the adjacent windows. The analysis window contains more than one event.

A modified form of an Autocorrelation transform of the type used for pitch detection in speech processing is applied to a single analysis window. This step is repeated for each analysis window.

The fundamental frequency is derived from the autocorrelation values of the analysis window. Usually the fundamental frequency is indicated by the largest autocorrelation value. This step is repeated for each analysis window.

A postprocessor is used to "smooth out" the results of all the individual analysis windows. The previously marked non-EIG segments (artifacts and silences) are added in this phase.

To produce the modified autocorrelation transform, the existing autocorrelation based algorithm was adapted to EIG in the following ways:

An improved algorithm was devised for determining pitch from the autocorrelation values. The algorithm usually chooses the highest autocorrelation peak (value). In EIG we found that sometimes the true pitch is not represented by a peak, but rather by a valley between several adjacent peaks. An algorithm was devised to locate those cases, and to correctly estimate the pitch. We refer to this phenomena as a "volcano" shaped autocorrelation graph, because the center of the "mountain" is found on lower ground.

A voiced/unvoiced decision mechanism was adapted from speech processing. The "unvoiced" EIG segments were defined as a non-signals (undecided segments). A postprocessor was used to decide on the pitch of those undecided segments. Although unvoiced speech segments do exist, "unvoiced" EIG segments are a virtual non-signal, and do not really exist.

A special pre-processing algorithm was devised. The signal undergoes convolution so as to increase the width of the event. This is unlike speech pre-processing, which is aimed at enhancing the high amplitude portions and/or filtering out the formants. This preprocessing technique is referred to as "fattening".

A very long analysis window of 4 seconds was used, in order to find frequencies ranging from 0.25 Hz to 5 Hz. In speech it is customary to use a window of about 30 milliseconds, in order to find frequencies ranging from 80 Hz to 300 Hz.

The invention also contemplates the use of a Segmented Autocorrelation algorithm. This is considered to be the best method for EIG, but other methods are also adequate. Segmented autocorrelation is described in "Pitch detection of speech signals using Segmented Autocorrelation"/I. A. Atkinson, A. M. Kondoz, B. G. Evans/Electronics Letters Vol. 31 No. 7 pp. 533–535/March 1995.

BRIEF DESCRIPTION OF THE DRAWINGS

The foregoing brief description, as well as further objects, features, and advantages of the present invention will be understood more completely from the following detailed description of a presently preferred embodiment, with reference being had to the accompanying drawings, in which:

FIG. 3, comprising FIG. 3A and FIG. 3B interfacing across line A—A in those figures, is a flowchart describing fundamental frequency estimation of an individual analysis window;

FIG. 4, comprising FIGS. 4A, 4B, 4C and 4D interfacing across lines A—A, B—B and C—C in those figures, is a flowchart expansion of one of the block 25 of FIG. 3 and describes the decision algorithm of the fundamental frequency estimator; and FIG. 5, comprising FIG. 5A and FIG. 5B interfacing across line A—A in those figures, is a flowchart describing the post-processing phase algorithms, which combine information from neighboring analysis windows in order to correct local estimation errors.

DETAILED DESCRIPTION OF THE PREFERRED EMBODIMENT

Figure 1:
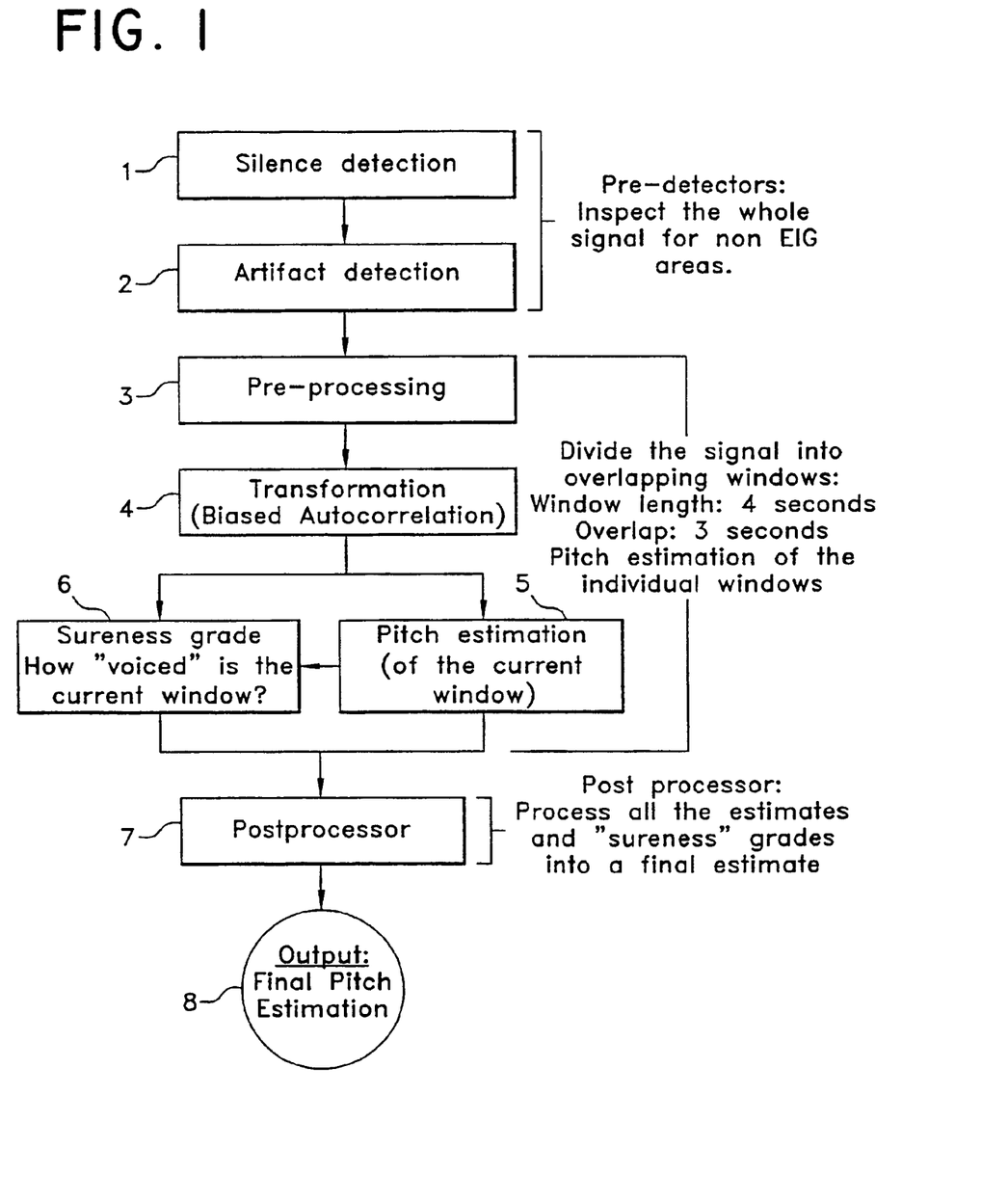
FIG. 1 is a functional block diagram showing an overview of the process of the preferred embodiment.

The preferred embodiment of the invention will now be described in detail with reference to the accompanying drawings. First a schematic overview of the preferred embodiment of a process and system for fundamental frequency estimation of EIG is presented in FIG. 1. The algorithm comprises of the following steps:

a. Detection of the non-EIG signals. The signal may include non-EIG segments, such as artifacts and silences. The signal is scanned and the non-EIG segments are marked and ignored. A silence detector 1 and an artifact detector 2 are used. An "artifact" is a dominant interference noise signal, which severely corrupts the EIG signal.

b. The signal is divided into overlapping analysis windows. Each window is 4 seconds long and has a 75% overlap with the adjacent windows. The analysis window must contain more than one event. It is contemplated that the analysis window could be as much as forty times the interval between successive events.

c. The autocorrelation transform 4 is applied to a single analysis window. This step is repeated for each analysis window. pre-processing 3 is optional, and is not used in the preferred embodiment.

d. The fundamental frequency is derived from the autocorrelation values of the analysis window 5. Usually the fundamental frequency is indicated by the largest autocorrelation value. A sureness measure 6 is computed for the estimated fundamental frequency of the analysis window. This step is repeated for each analysis window.

e. A postprocessor 7 is used to "smooth out" the results of all the individual analysis windows. The previously marked non-EIG segments (artifacts and silences) are added in this phase.

f. The output is the estimated fundamental frequency of the signal 8.

The preferred embodiment of the invention includes software which preferably runs on a Pentium PC, using the Windows 95 operating system. The algorithm was implemented on the "Matlab" software by "The Mathworks Inc."

The algorithm was written in the Matlab language, and runs within the Matlab program shell. It also requires the "Digital Signal Processing Toolbox" for Matlab, by "The Mathworks Inc."

Figure 2:
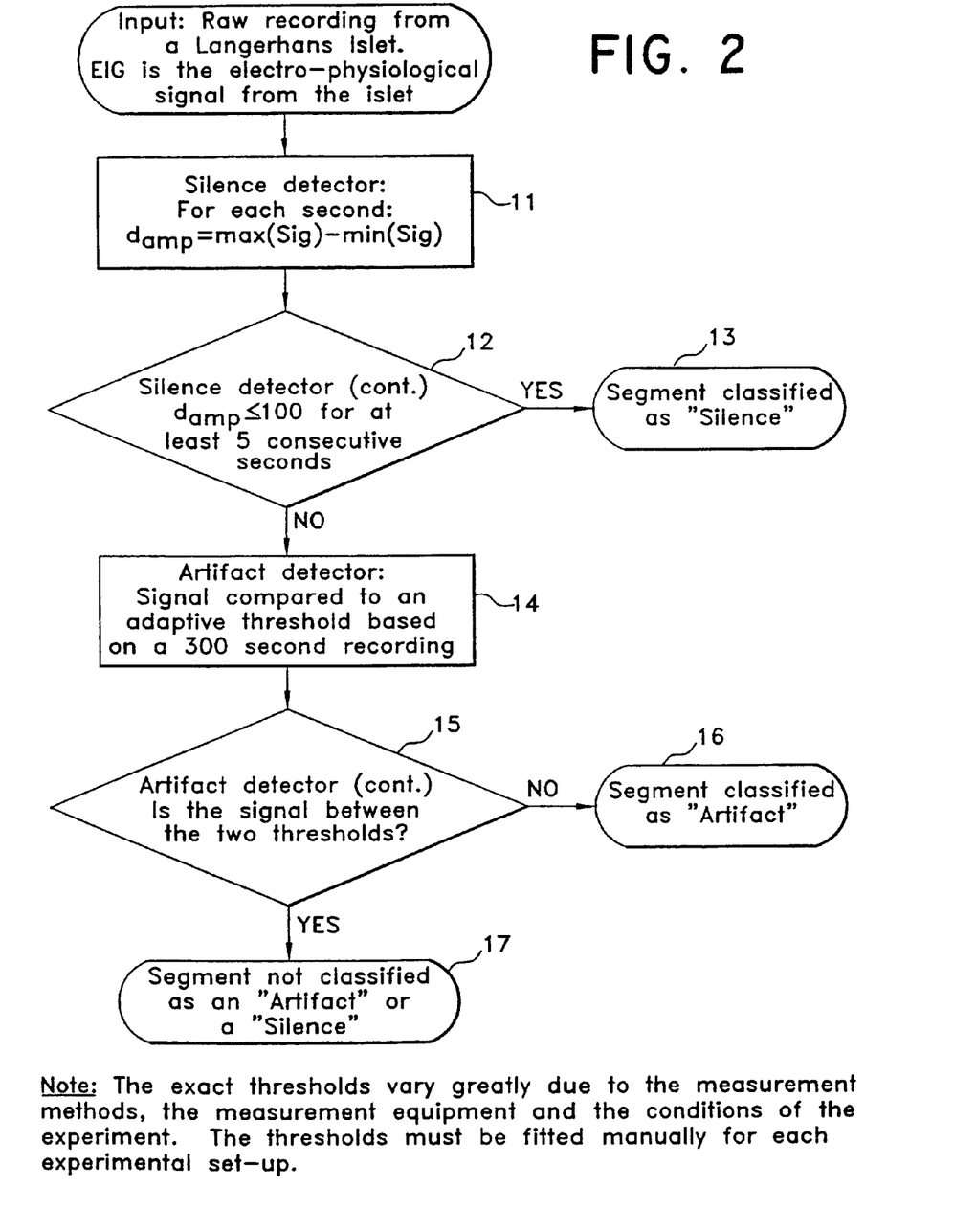
FIG. 2 is a flowchart describing the pre-detectors, the silence detector and the artifact detector.

FIG. 2. is a flowchart describing the pre-detectors. The silence detector (11, 12,13) involves two steps. In the first step 11 an amplitude related measure is computed for each second, and in the second step 12 the amplitude related measure is compared to a fixed threshold. "Sig" is the raw digital input signal. It is the raw signal recorded from the islet, after an Analog to Digital conversion. In block 11 each one second window is examined. "Max(Sig)" is the maximum sample value within the examined one second window. "Min(Sig)" is the minimum of the samples' values within the examined one second window. As "Sig" is always a real number, the real maximum and minimum are computed. If the measure is below the threshold for more than 5 seconds, then the segment is classified as silence 13. The threshold depends on the measurement equipment and environment. It also depends on the digitizing scale. In the preferred embodiment the maximum amplitude of the EIG signal is approximately 4000 amplitude units, so a threshold of 100 amplitude units is used. An "amplitude unit" is the amplitude difference between two adjacent quantization levels of the Analog to Digital converter. In the preferred embodiment one "amplitude unit" corresponds to 0.25 Micro-Volt of the original electrical signal. "Original" means before amplification.

The artifact detector (14, 15, 16, 17) involves two steps. In the first step 14 the signal is compared to an adaptive threshold. The adaptive threshold is computed using a 300 second long recording, by the following computation:

A high reference is defined as the 99.833 percentile of the histogram of the amplitude values of the 300 second long recording.

A low reference is defined as the 0.167 percentile of the histogram of the amplitude values of the 300 second long recording.

An amplitude reference is defined as the high reference minus the low reference.

A high threshold is defined as the high reference plus the amplitude reference.

A low threshold is defined as the low reference minus the amplitude reference.

The "histogram" used in block 14 is generated by simply sorting all the sample values ("amplitudes") of a 300 second long recording. The sorting is done from the smallest value to the largest value. Based on those sorted values the two references are derived. The "high reference" is the 99.833 percentile of the sorted values. The "low reference" is the 0.167 percentile of the sorted values. The term "histogram" refers to the sorting of the values, and can be replaced by the term "sorted amplitude values."

The second step 15 involves checking whether there are samples in which the signal's amplitude is above the high threshold or below the low threshold. If such samples are found then they are classified as containing an artifact 16. The remaining samples 17 are not classified as an artifact or as a silence.

Figure 3A:
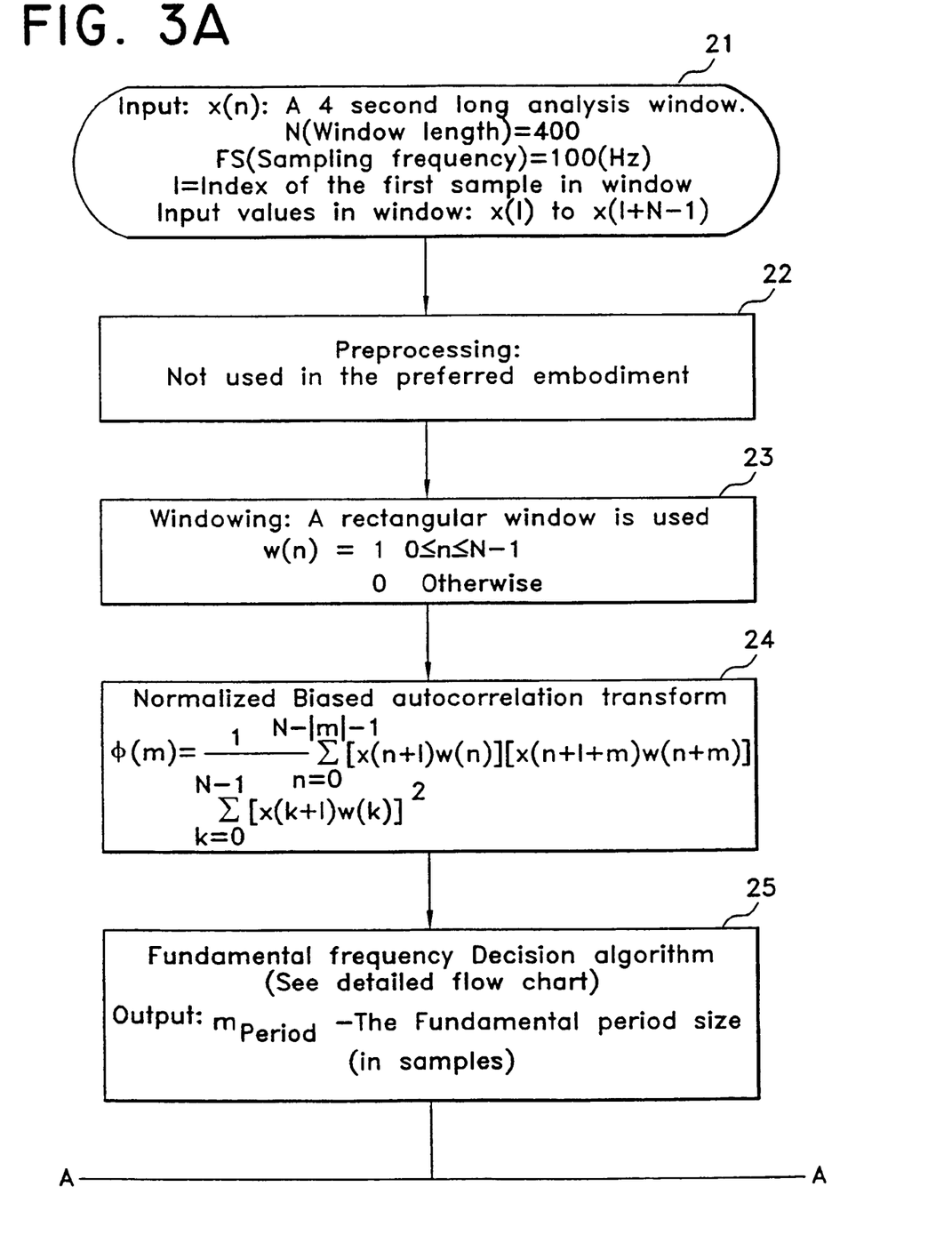
Figure 3B:
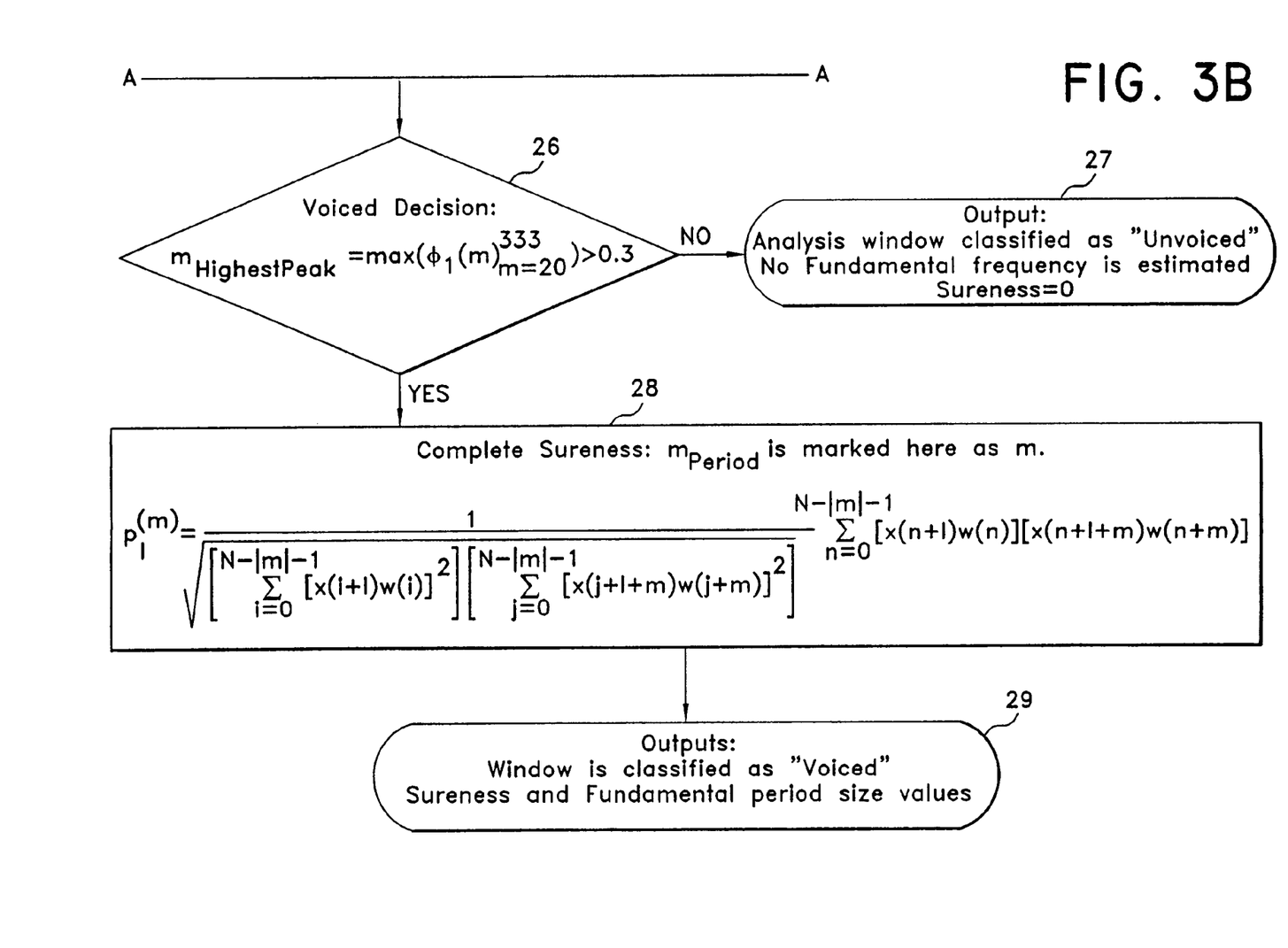
Figure 4A:
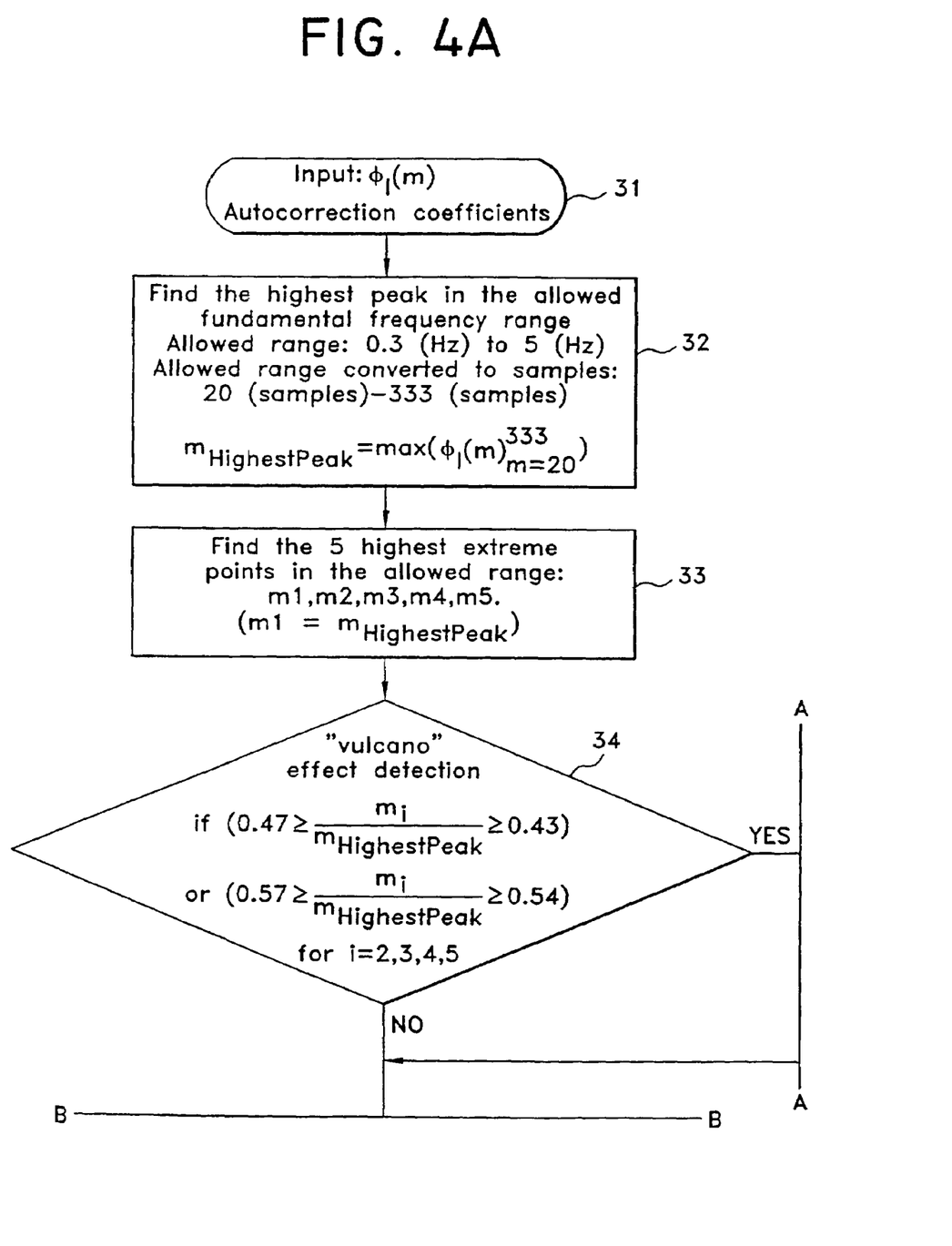
Figure 4B:
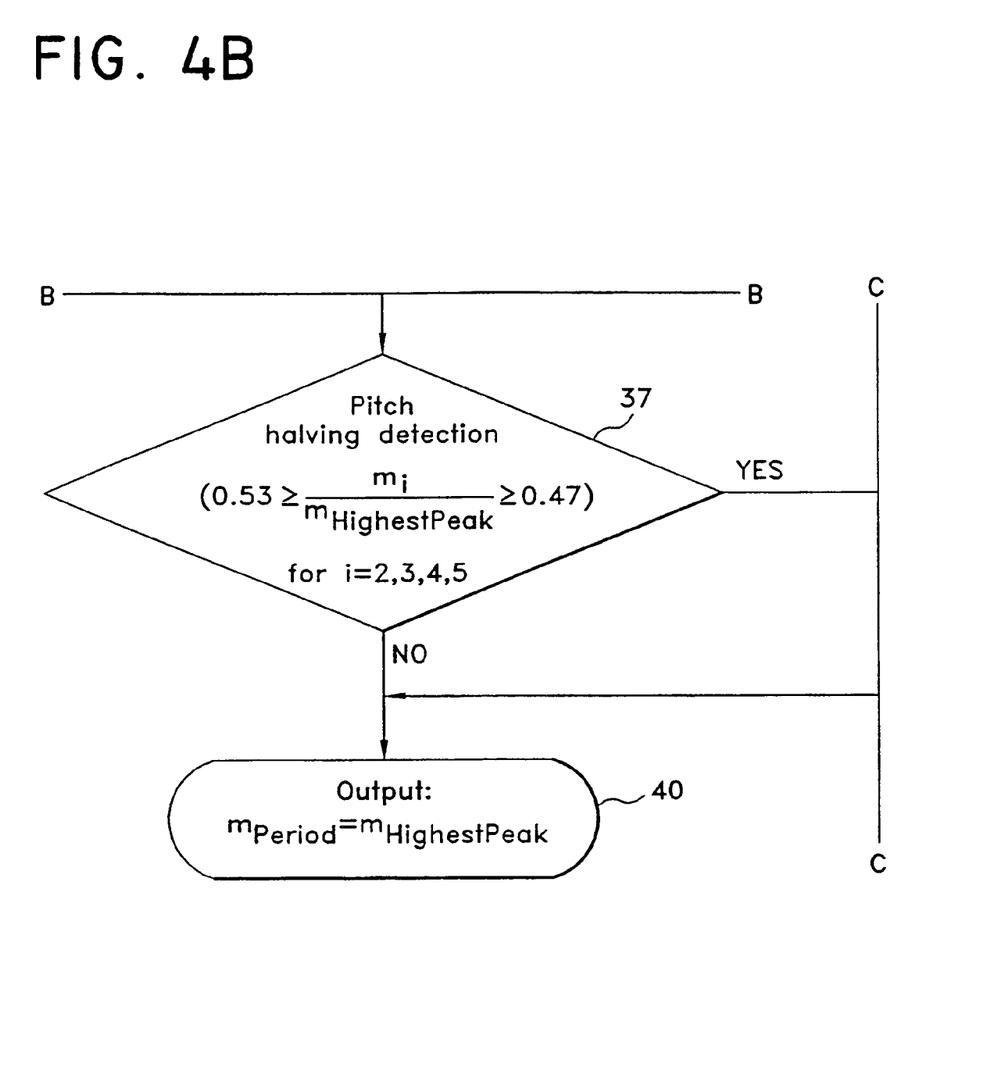
Figure 4C:
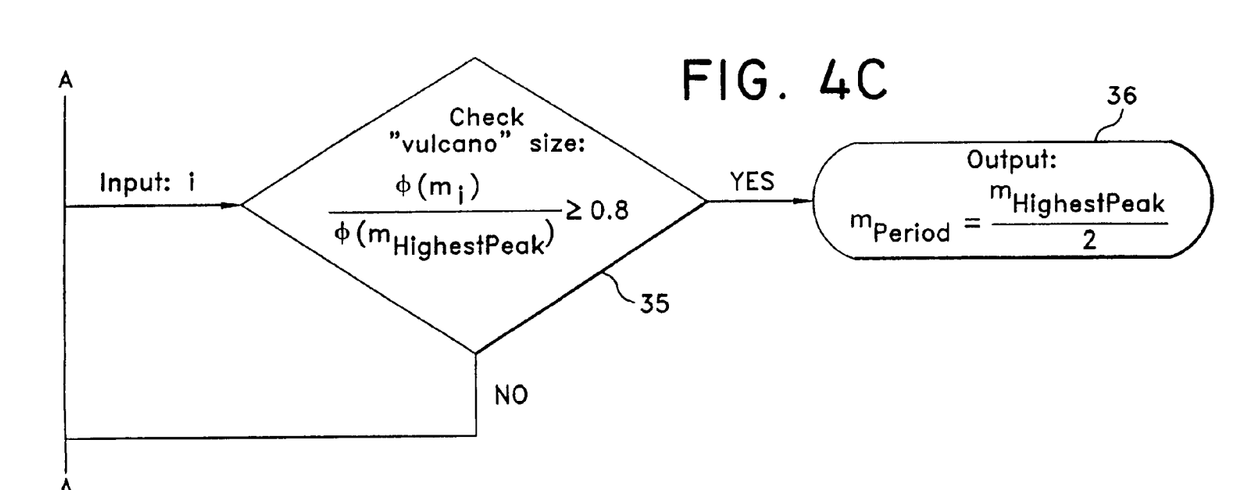
Figure 4D:
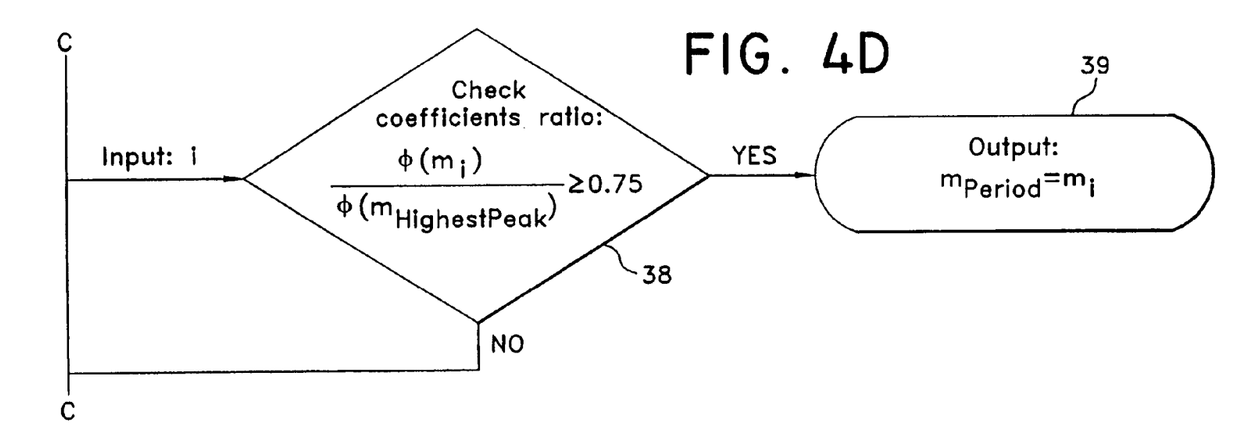

FIG. 3 contains a flowchart describing the steps that are performed on each analysis window. Each analysis window is 4 seconds long. Overlapping analysis windows are used. There is a 3 second overlap between two successive windows. Analysis windows containing either silences or artifacts are not analyzed. The analysis windows are described in block 21, and are represented mathematically by the following notation:

x(n) are the raw digital samples of the signal. We earlier referred to this raw input signal as "Sig." This is the same signal, only that here a more strict mathematical notation is used. The analysis window contains 4 seconds of signal. The sampling frequency ("FS") in the preferred embodiment is 100 Hz, therefore the analysis window contains 400 samples. This is marked by "N(Window length)=400. " The first sample in the analysis window is x(l), where "l" is the index of the sample. Therefore the last sample in the analysis window is x(l+399)=x(l+N−1). Therefore the analysis window is described by the samples it contains from x(l) to x(l+N−1).

Preprocessing 22 may be used, but it is not implemented in the preferred embodiment.

A rectangular window 23 is applied to the samples, and a normalized biased autocorrelation transform 24 is computed. It is represented mathematically by the following equation:

$$\varphi(m) = \frac{1}{\sum_{k=0}^{N-1}[x(k+1)w(k)]^2} \sum_{n=0}^{N-|m|-1}[x(n+1)w(n)][x(n+l+m)w(n+m)] \quad (I)$$

where "w(n)" is the windowing function." As "w(n)" is a rectangular window, as described in block 23, it is equivalent to "1" within the analysis window:

w(n)=1 0≦n≦N−1

0 Otherwise

The autocorrelation transform is further described in the book "Digital Processing of Speech Signals", L. R. Rabiner and R. W. Schafer, 1978, pp. 141–164. The fundamental frequency decision algorithm 25 is described in more detail in FIG. 4.

We will now refer to FIG. 4 and later return to FIG. 3.

FIG. 4 is a flowchart describing the fundamental frequency decision algorithm. Actually it decides on the fundamental period, from which the fundamental frequency can be derived. An improved algorithm was devised for determining the fundamental frequency from the autocorrelation values. In typical algorithms the highest autocorrelation peak (value) is usually chosen. In EIG, it was found that sometimes the true pitch is not represented by a peak, but rather by a valley between several adjacent peaks. An algorithm was devised to locate those cases, and to estimate the pitch correctly. We refer to this phenomenon as a "volcano" shaped autocorrelation graph, because the center of the "mountain" is found on lower ground.

The input to the decision algorithm is a vector containing the autocorrelation coefficients 31. Steps 32 and 33 find the 5 highest extreme points within the allowed frequency range. A "volcano" effect detector 34 checks first whether one of the highest peaks is found in a suspected "volcano" area. If such a peak is found, it's index (i) is passed on in order to check the peak's amplitude 35 compared to the amplitude of the highest peak. If the result is positive then a "volcano" is detected 36 and the estimated fundamental period is half of the autocorrelation lag corresponding to the highest peak. The autocorrelation is represented by equation (1) above. m is the "autocorrelation lag." It is the lag between the two segments on which the correlation is computed. The first segment is x(n+l) to x(n+l+N−|m|−1) and the second segment is x(n+l+m) to (x+l+m+N−|m|−1). Also, see "Digital Processing of Speech Signals", L. R. Rabiner and R. W. Schafer, 1978, pp. 141–164.

A pitch halving detection algorithm 37 first checks the ratio of the autocorrelation coefficients' lag 37, and then their amplitudes 38. If one of the highest peaks fulfills both those conditions then it is chosen as the estimated fundamental period 39. If both the "volcano" detector and the pitch halving detector produced negative results, then the estimated fundamental period is assumed to be the lag of the highest autocorrelation peak 40. The output of the fundamental period decision algorithm of FIG. 4 is the estimated fundamental period. This output is returned to block 26 in FIG. 3.

A "voiced" decision mechanism 26 (FIG. 3) is used to decide whether the fundamental frequency should be estimated in the current analysis window. If the maximum autocorrelation coefficient in the allowed lag range (a lag of 20 to 333 samples) is below 0.3, then the analysis window is classified as "unvoiced", and no fundamental frequency is estimated 27. In that case a sureness grade of zero is given to the analysis window.

The voiced/unvoiced decision mechanism was adapted from speech processing. The "unvoiced" EIG segments were defined as non-signals (undecided segments). The postprocessor will be used in later stages to decide on the fundamental frequency of those undecided segments. Note that unvoiced speech segments do exist, while "unvoiced" EIG segments are a virtual non-signal, and do not really exist.

If the current analysis window is not classified as "unvoiced" then the estimation process continues, and a sureness grade is calculated for the current analysis window 28. A higher sureness grade indicates that there is a higher probability that the fundamental frequency was estimated correctly. For each analysis window several outputs 29 are returned:

1. The estimated fundamental period—this value is not returned if the analysis window is classified as "unvoiced";
2. A "voiced"/"unvoiced" decision—specifies whether the fundamental period was estimated in the analysis window; and
3. A sureness grade—this value is not returned if the analysis window is classified as "unvoiced".

Figure 5A:
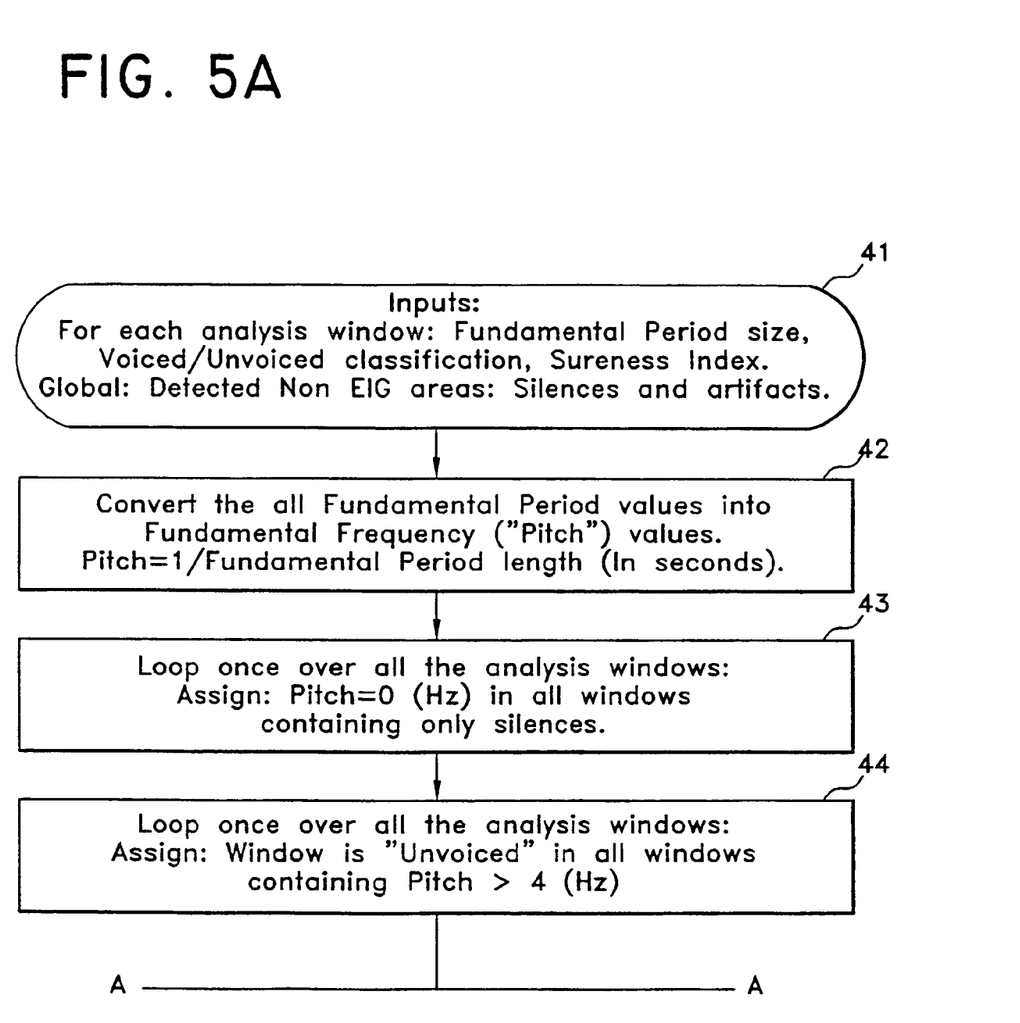
Figure 5B:
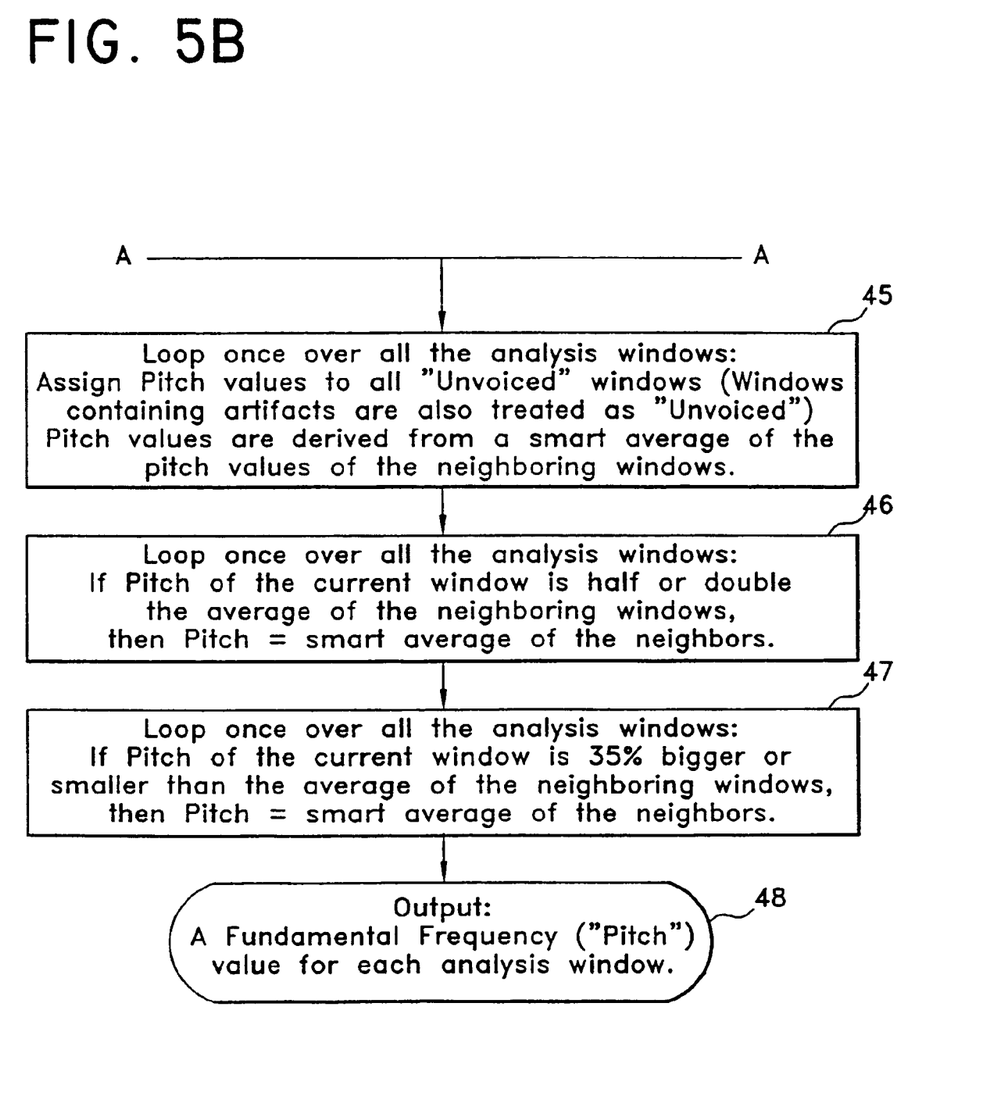

FIG. 5 describes the final stage of the estimation process: the postprocessor. The postprocessor combines all the acquired data 41 into a fundamental frequency estimate of the raw signal. The postprocessor operates on a 300 second long recording of the raw signal. The first step 42 is to convert all the estimated fundamental period values into estimated fundamental frequency ("Pitch") values. The output of this stage is a fundamental frequency estimate, in Hertz, for every "voiced" analysis window. The next step 43 inserts the previously detected silence segments 1 into the fundamental frequency estimation results. The fundamental frequency is assigned a value of 0 (Hz) in all windows containing only silences. All analysis windows containing an unlikely fundamental frequency estimate are marked as "unvoiced" in the next step 44.

The next step 45 assigns a fundamental frequency ("pitch") value to the "unvoiced" segments. The postprocessor loops once over all the analysis windows. It assigns Pitch values to all "unvoiced" windows (windows containing artifacts are also treated as "unvoiced"). Pitch values are derived from an average of the pitch values of the neighboring windows. Some minor data dependent modifications can be added in order to create a smarter averaging method, but those are minor changes which are very data dependent. A pitch halving/doubling error correcting mechanism is then applied 46. The algorithm loops once over all the analysis windows. If the Pitch of the current window is half or double the average of the neighboring windows, then the current Pitch is taken as a smart average of the neighbors. The term "smart averaging" refers to the average of an ensemble of numbers, after the extreme values are removed. For example: We can define a "smart average" of 8 numbers in the following way:

1. Remove the maximal and minimal numbers and
2. Compute the average of the remaining 6 numbers.

This "smart averaging" method is used in order to achieve more stable and robust results.

The final step 47 looks for an analysis window having a pitch which is significantly different than its neighbors. The algorithm loops once over all the analysis windows. If the Pitch of the current window, is 35% greater or smaller than the average of the neighboring windows, then the current Pitch is taken as a smart average of the neighbors.

The final output 48 of the entire fundamental frequency estimation process is a fundamental frequency value for each analysis window.

Although a preferred embodiment of the invention has been disclosed for illustrative purposes, those skilled in the art will appreciate that many additions, modifications and substitutions are possible without departing from the scope and spirit of the invention. For example, the principles and applications of the invention are not limited to the particular biological phenomenon described. They could be utilized equally well, for example, for measuring an optical signal from living cells of a muscle or the electrical signals of neurons, or various signals produced by similar or other biological micro-structures. In particular, it is contemplated that the invention could find utility in any application where a cell or other biological micro-structure is moved outside its natural environment and used as a biological sensor.

I claim:

1. A method for monitoring biological micro-structure activity which produces detectable signals characterizing events, comprising the steps of estimating the fundamental frequency of the occurrence of events from the detectable signals, without detecting the occurrence of individual events, wherein the estimating step includes performing an autocorrelation operation and locating and estimating a pitch that is represented by a valley between adjacent autocorrelation peaks.

2. The method of claim 1 wherein events are analyzed during an analysis window which spans more than one event.

3. The method of claim 2, wherein an analysis window spans a duration of up to 40 times the interval between successive events.

4. The method of claim 1, wherein the events are signals produced by biological micro-structures which are displaced from their original environment.

5. The method of claim 1, wherein the events are signals produced by living cells.

6. The method of claim 5 wherein the events are signals produced by the Islets of Langerhans.

7. The method of claim 1 further comprising the step of using the fundamental frequency as a measure of a blood or tissue constituent level of a patient.

8. The method of claim 7 wherein the blood constituent level is the blood glucose level in the vicinity of the biological micro-structure.

9. The method of claim 1 wherein the events are electrical signals produced by living cells in the Islets of Langerhans used as a probe within a patient and the fundamental frequency estimate is used as a measure of blood glucose level of the patient.

10. In a system for monitoring biological micro-structure activity which produces detectable signals characterizing events, a sensor capable of receiving the sensible signals and a processor including a module for estimating the fundamental frequency of the occurrence of events from the detectable signals, without first detecting the occurrence of individual events, wherein the module for estimating the fundamental frequency includes components configured to perform an autocorrelation operation and to locate and estimate a pitch that is represented by a valley between adjacent autocorrelation peaks.

11. The system of claim 10 wherein the processor further comprises a module for producing an analysis window during which events are analyzed, the analysis window spanning more than one event.

12. The system of claim 11, wherein an analysis window spans a duration of up to 40 times the interval between successive events.

13. The system of claim 10, wherein the sensor is a probe capable of detecting signals emitted by living cells in the Islets of Langerhans, the frequency estimate being an indication of blood glucose level of a patient in which those cells are present.

14. The system of claim 10, wherein the sensor is a probe capable of detecting signals emitted by living cells in the Islets of Langerhans.

15. The system of claim 10, wherein the module for estimating further includes one of the following submodules:

a submodule which identifies "unvoiced" segments of the detectable signal as undecided as to pitch, the pitch of those segments being estimated by a subsequent processing submodule;

a submodule which controls the analysis window to have a duration in the range of 0.25 to 5 Hertz;

a submodule controlling the analysis window to have a duration in the range of several seconds; and a submodule performing a pre-processing operation which has the effect of increasing the effective duration of an event.

\* \* \* \* \*